(12) United States Patent
Moszner et al.

(10) Patent No.: US 9,861,557 B2
(45) Date of Patent: Jan. 9, 2018

(54) DENTAL MATERIALS ON THE BASIS OF UREA GROUP-CONTAINING MONOMERS

(71) Applicant: Ivoclar Vivadent AG, Schaan (LI)

(72) Inventors: Norbert Moszner, Mauren (LI); Yohann Catel, Sargans (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/904,129

(22) PCT Filed: Jul. 11, 2014

(86) PCT No.: PCT/EP2014/001905
§ 371 (c)(1),
(2) Date: Jan. 11, 2016

(87) PCT Pub. No.: WO2015/003812
PCT Pub. Date: Jan. 15, 2015

(65) Prior Publication Data
US 2016/0151249 A1    Jun. 2, 2016

(30) Foreign Application Priority Data

Jul. 12, 2013    (EP) .................................... 13176333

(51) Int. Cl.
*A61K 6/083*    (2006.01)
*A61K 6/00*    (2006.01)

(52) U.S. Cl.
CPC ............ *A61K 6/083* (2013.01); *A61K 6/0017* (2013.01); *A61K 6/0023* (2013.01); *A61K 6/0052* (2013.01)

(58) Field of Classification Search
CPC .................................................... A61K 6/083
See application file for complete search history.

(56) References Cited

U.S. PATENT DOCUMENTS 3,488,330 A    1/1970    Szita et al.
4,744,827 A    5/1988    Winkel et al.
5,070,165 A    12/1991    Muller et al.
5,292,619 A    3/1994    Okinoshima et al.
6,943,211 B1    9/2005    Hubbell et al.
2011/0053116 A1    3/2011    Hecht et al.
2011/0281025 A1    11/2011    Arai et al.
2013/0109780 A1    5/2013    Karim et al.

OTHER PUBLICATIONS

International Preliminary Report on Patentability of PCT/EP2014/001905, Jan. 12, 2016, 7 pages.
Moszner, N. et al., "New Polymer-Chemical Developments in Clinical Dental Polymer Materials: Enamel-Dentin Adhesives and Restorative Composites," Journal of Polymer Science, 2012 (50), 4369-4402, Wiley Periodicals, Inc.
Moszner, N. et al., "Chemical aspects of self-etching enamel-dentin adhesives: A systematic review," J. Dental Materials, 2005 (21), 895-910, Elsevier Ltd.
Dubosclard-Gottardi, C. et al., "New Selective Syntheses of (Meth)Acrylic Monomers: Isocyanates, Isocyanurates, Carbamates and Ureas Derivatives," Tetrahedron, vol. 51, No. 9, pp. 2561-2572, 1995, Great Britain.
Galt, H. et al., "Facile Ring-Opening Reactions of Phthalimides as a New Strategy to Synthesize Amide-Functionalized Phosphonates, Primary Phosphines, and Bisphosphines," J. Org. Chem., 2000, 65, 676-680.

*Primary Examiner* — Michael Pepitone
(74) *Attorney, Agent, or Firm* — Ann M. Knab; Thad McMurray

(57) ABSTRACT

Dental material which contains a urea derivative according to general formula I,

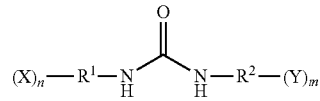

Formula I in which $R^1$ and $R^2$ are in each case independently of each other an aliphatic $C_1$-$C_{15}$ radical which can be interrupted by —O—, —S—, —CO—O—; X is a radically polymerizable group; Y is a radically polymerizable group or an acid group; n, m are in each case independently of each other 1, 2, or 3.

16 Claims, No Drawings

DENTAL MATERIALS ON THE BASIS OF UREA GROUP-CONTAINING MONOMERS

CROSS-REFERENCE TO RELATED APPLICATIONS

This application is a National Stage application of International Patent Application No. PCT/EP2014/001905 filed on Jul. 11, 2014, which claims priority to European Patent Application No. 13176333.6 filed on Jul. 12, 2013, the disclosures of which are incorporated herein by reference in their entirety.

The present invention relates to dental materials based on monomers containing urea groups. The dental materials are particularly suitable as tooth filling materials (composites), adhesives, cements or coating materials.

The polymerizable organic matrix of dental adhesives, cements or composites primarily consists of a mixture of monomers, initiator components, stabilizers and pigments. Mixtures of dimethacrylates are usually used as resins (N. Moszner, T. Hirt, J. Polym. Sci. Part A: Polym. Chem. 50 (2012) 4369-4402).

In the case of matrix monomers, a distinction is drawn between non-acidic and acidic monomethacrylates, cross-linking dimethacrylates and multifunctional methacrylates. Radically polymerizable monomers with acid groups give dental materials self-etching properties, with the result that an acid treatment of the tooth surface before application of the materials for etching the tooth surface and for removing the so-called smear layer can be avoided. They also improve the adhesion to the tooth, through ionic or covalent interactions with the tooth substance. They are primarily used in adhesives and self-etching dental materials (N. Moszner, U. Salz, J. Zimmermann, Dent. Mat. 21 (2005) 895-910).

The bonding of the radically polymerizable group(s) to the molecule takes place in the case of known dental monomers mainly via ester, ether and urethane groups. However, monomers are also known in which the bonding takes place via other groups, such as for example urea groups.

Dental materials based on polymerizable tricyclodecane derivatives are known from EP 0 209 700 A2. The tricyclodecane derivatives have two (meth)acrylic acid groups which are bound to the tricyclodecane radical via urethane or urea groups.

EP 0 400 383 A1 discloses (meth)acrylic acid derivatives, containing urea groups, of triisocyanates. These are said to be suitable for use in dental materials. The (meth)acrylic acid derivatives have a bicyclic base body such as diphenylmethane or dicyclohexylmethane.

WO 2009/006282 A2 relates to dental materials based on polyfunctional (meth)acrylates which contain urea, amide or preferably urethane groups.

WO 2008/033911 A2 discloses radically polymerizable monomers which can contain urea groups and which are used as gelling agents in dental compositions. By gelling agents are meant low-molecular-weight substances which form a three-dimensional network when they are dissolved in an organic liquid, and which immobilize the liquid, forming a non-flowable gel. The gel can be reversibly liquefied by increasing the temperature.

Of the named documents, only WO 2008/033911 A2 describes specific dental materials that contain monomers containing urea groups. Through self-organization, these monomers form physical networks which solidify the composition and result in a gel with waxy properties. Gel formation is disadvantageous for many forms of use because it is associated with a dramatic increase in viscosity, which makes e.g. the use of composites and adhesives much more difficult. Gel formation also has a disadvantageous effect on the polymerization rate.

Dental materials must satisfy a large number of different requirements. They must have a good long-term stability vis-à-vis premature curing during storage, but on the other hand they must also display a high polymerization rate in radical homo- and copolymerization. They are to be stable and light-resistant under oral conditions and are not to tend towards discolorations. In addition, they are to have a low oral toxicity and only a low shrinkage during polymerization. Moreover, the water sorption after curing is to be small, however in particular in the case of adhesives a good miscibility with polar solvents and mixtures thereof with water before curing is advantageous.

Known dental materials contain monomers which have been optimized in respect of particular properties. Monomers which satisfy all the requirements in the same way are not known, with the result that there is still a need for improved matrix monomers. Until now, monomers containing urea groups have not been used in practice.

The object of the invention is to provide dental materials which satisfy the named requirements and have a profile of properties that is optimal for dental purposes, and in particular have a high polymerization rate in radical polymerization. In addition, the dental materials are to have good mechanical properties after polymerization. They are also to have a high adhesion to the tooth structure (dentine and in particular enamel), and to be particularly suitable as adhesives, cements, composites or coating materials. Moreover, a good solubility in polar solvents and in mixtures of polar solvents and water is also desirable.

The object is achieved according to the invention by dental materials which contain at least one urea derivative according to general formula I,

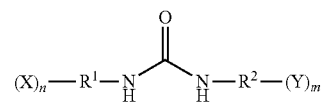

Formula I in which $R^1$, $R^2$=in each case independently of each other an aliphatic $C_1$-$C_{15}$ radical which can be interrupted by —O—, —S—, —CO—O—, X=a radically polymerizable group, Y=a radically polymerizable group or an acid group, n, m=in each case independently of each other 1, 2 or 3.

Preferred radically polymerizable groups are $CH_2$=$CR^3$—CO—Z— or $R^4$O—CO—C(=$CH_2$)—$CH_2$—Z—, wherein Z is O or $NR^5$ or is absent, $R^3$ is H or $CH_3$ and $R^4$ and $R^5$ are in each case independently of each other H or $C_1$-$C_7$ alkyl. (Meth)acryloyloxy groups ($CH_2$=$CR^3$—CO—Z— with Z=O) are particularly preferred, in particular (meth)acryloylamino groups ($CH_2$=$CR^3$—CO—Z— with Z=$NR^5$) and $R^4$O—CO—C(=$CH_2$)—$CH_2$—Z—, wherein Z is preferably O; $R^3$ is in each case H or $CH_3$ and $R^4$ and $R^5$ are in each case independently of each other $CH_3$ or $C_2H_5$.

Preferred acid groups are —PO(OH)$_2$, —PO(OH)$_2$ and —SO$_3$H.

According to a particularly preferred embodiment, X and Y have the following meanings:

$X=CH_2=CR^3—CO—Z—$ or $R^4O—CO—C(=CH_2)—CH_2—Z—$, wherein Z is O or $NR^5$ or is absent, $R^3$ is H or $CH_3$ and $R^4$ and $R^5$ are in each case independently of each other H or $C_1$-$C_7$ alkyl, and $Y=$either $CH_2=CR^{3'}—CO—Z'—$ or $R^{4'}O—CO—C(=CH_2)—CH_2—Z'—$, wherein $Z'$ is O or $NR^{5'}$ or is absent, $R^{3'}$ is H or $CH_3$ and $R^{4'}$ and $R^{5'}$ are in each case independently of each other H or $C_1$-$C_7$ alkyl; or $—PO(OH)_2$, $—O—PO(OH)_2$, $—SO_3H$.

The groups $R^1$ and $R^2$ are aliphatic groups which are substituted n times by the radical X or, respectively, m times by Y. These groups can be branched or straight-chained. Formula I covers only those compounds which are compatible with the theory of chemical valence.

$R^1$ and $R^2$ are preferably linear aliphatic radicals, in particular radicals with the formula $(CH_2)_p$ wherein p is an integer from 1 to 15, particularly preferably 2 to 12 and quite particularly preferably 3 to 10. $R^1$ and $R^2$ can be different or preferably identical. Linear radicals are particularly preferred in each case when n and m are 1. When n and m are greater than 1, $R^1$ and $R^2$ preferably have a branched structure. In this case, the several groups X and Y are preferably distributed onto the main and side chain(s).

The indication that a radical is interrupted by heteroatoms or functional groups is to be understood such that the heteroatoms or functional groups are inserted into the carbon chain and are bordered on both sides by C atoms. The stringing together of heteroatoms and/or functional groups does not come under this definition.

Preferably, $R^1$ is not interrupted or is interrupted by 1 to 4, in particular 1 to 2, heteroatoms or functional groups, particularly preferably by 1 or 2 O atoms. $R^2$ is preferably not interrupted or is interrupted by 1 to 4, in particular 1 to 2, heteroatoms or functional groups, particularly preferably by 1 or 2 O atoms.

The preferred definitions of the variables named herein can be chosen independently of one another. According to the invention, however, compounds in which all the variables have one of the preferred and in particular one of the particularly preferred definitions are naturally particularly preferred.

Dental materials which contain a compound of Formula I in which Y is an acid group are particularly suitable as self-etching materials, in particular as adhesives, cements, and fissure sealants. Preferred acidic urea derivatives are compounds in which the variables of Formula I have the following meanings:

$R^1=$an aliphatic $C_2$-$C_{12}$ radical which can be interrupted by $—O—$ or $—CO—O—$,
$R^2=$an aliphatic $C_1$-$C_{10}$ radical which can be interrupted by $—O—$ or $—CO—O—$,
$X=CH_2=CR^3—CO—Z—$ or $R^4O—CO—C(=CH_2)—CH_2—Z—$, wherein Z is O or $NR^5$, $R^3$ is H or $CH_3$ and $R^4$ and $R^5$ are in each case independently of each other H or $C_1$-$C_3$ alkyl,
$Y=—PO(OH)_2$, $—O—PO(OH)_2$, $—SO_3H$,
n=1 or 2,
m=1 or 2.

Particularly preferred are dental materials of this embodiment in which the variables have the following meanings:
$R^1$, $R^2=$in each case independently of each other a linear aliphatic $C_2$-$C_{10}$ radical which can be interrupted by 1 or 2 $—O—$, wherein $R^1$ and $R^2$ are preferably identical,
$X=CH_2=CR^3—CO—Z—$, wherein Z is O or $NR^5$, or $R^4O—CO—C(=CH_2)—CH_2—Z—$, wherein $Z=O$, $R^3$ is H or $CH_3$, $R^4$ is methyl or ethyl and $R^5$ is H, methyl or ethyl,
$Y=—PO(OH)_2$, $—O—PO(OH)_2$, $—SO_3H$,
n, m=in each case 1.

According to a further embodiment, Y is a radically polymerizable group. In such cases, the urea derivatives of Formula I have cross-linking properties. Dental materials which contain such cross-linking derivatives are particularly suitable as adhesives, coating materials, cements or filling materials (composites), in particular as adhesives and cements. Preferred cross-linking urea derivatives of Formula I are compounds in which the variables have the following meanings:

$R^1=$an aliphatic $C_2$-$C_{12}$ radical which can be interrupted by $—O—$ or $—CO—O—$,
$R^2=$an aliphatic $C_1$-$C_{10}$ radical which can be interrupted by $—O—$ or $—CO—O—$,
X, Y=in each case independently of each other $CH_2=CR^3—CO—Z—$ or $R^4O—CO—C(=CH_2)—CH_2—Z—$, wherein Z is O or $NR^5$, $R^3$ is H or $CH_3$ and $R^4$ and $R^5$ are in each case independently of each other H or $C_1$-$C_3$ alkyl, wherein X and Y are preferably identical,
n=1 or 2,
m=1 or 2; particularly preferably:
$R^1$, $R^2=$in each case independently of each other a linear aliphatic $C_2$-$C_{10}$ radical which can be interrupted by 1 or 2 $—O—$, wherein $R^1$ and $R^2$ are preferably identical,
X, Y=in each case independently of each other $CH_2=CR^3—CO—Z—$, wherein Z is O or $NR^5$, or $R^4O—CO—C(=CH_2)—CH_2—Z—$, wherein $Z=O$, $R^3$ is H or $CH_3$ and $R^4$ is methyl or ethyl and $R^5$ is H, methyl or ethyl, wherein X and Y are preferably identical,
n, m=in each case 1.

Urea derivatives in which Y is an acid group and n is greater than 1 also have, in addition to the self-etching and adhesion-promoting action of the acid groups, cross-linking properties and can be used as cross-linking agents. However, acidic urea derivatives of Formula I with only one polymerizable group can advantageously also be combined with non-acidic urea derivatives of Formula I which have two or more polymerizable groups. Compositions which contain at the same time cross-linking and acidic urea derivatives of Formula I are particularly preferred according to the invention.

The polymerizable urea group containing monomers of general formula I can be easily prepared. For example, it is possible to react $NH_2$-functionalized polymerizable (meth)acrylates or (methacryl) amides and $NH_2$-functionalized phosphonates, phosphates or sulphonates with isocyanate-functionalized polymerizable (meth)acrylates or (methacryl) amides, wherein in the case of phosphonates, phosphates or sulphonates the release of the acid groups subsequently takes place and the compounds of general formula I form. The $NH_2$-functionalized polymerizable (meth)acrylates or (methacryl) amides can be prepared by (meth)acrylation of corresponding OH-protected amino alcohols followed by splitting off of the protective group or of corresponding diamines respectively. $NH_2$-functionalized phosphonates can be obtained for example starting from α, ω-dihalogenalkanes by an Arbuzov reaction at one end of the molecule followed by a Gabriel reaction at the second halogen atom. Isocyanate-functionalized polymerizable (meth)acrylates or (methacryl) amides can be prepared by reacting corresponding bromoalkyl (meth)acrylates or bromoalkyl (meth)acrylamides respectively with alkali cyanates (cf. C. Dubosclard-Gottardi, P. Caubere, Y Fort Tetrahedron 51 (1995) 2561-2572):

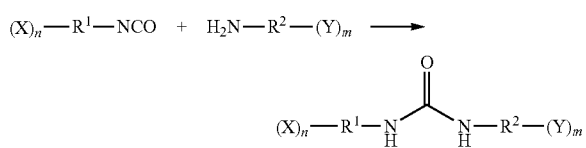

Specifically, compounds of Formula I in which X and Y are radically polymerizable groups can be obtained e.g. by reacting 2-isocyanatoethyl methacrylate with 5-aminopentyl methacrylamide:

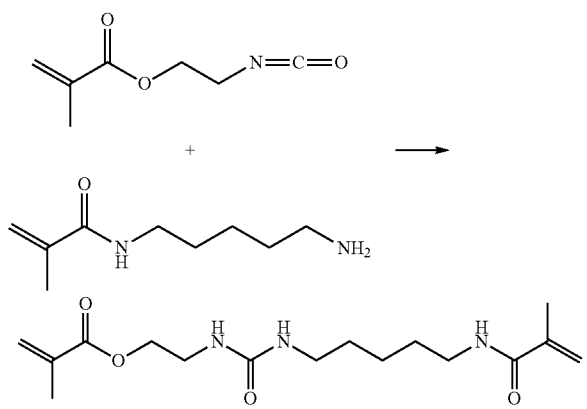

Urea derivatives in which Y is an acid group can be prepared for example by reacting 2-isocyanatobutyl methacrylate with 5-aminopentylphosphonic acid diethyl ester and then release of the phosphonic acid group:

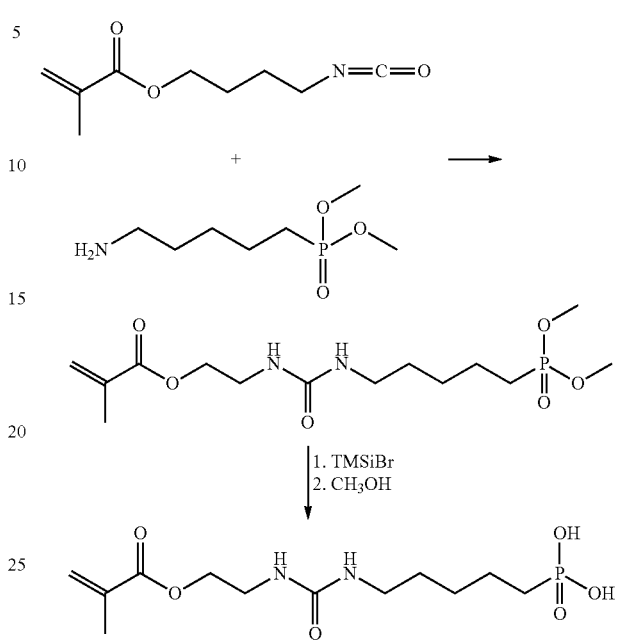

Preferred examples of the polymerizable monomers containing urea groups, according to the invention, of general formula I are:

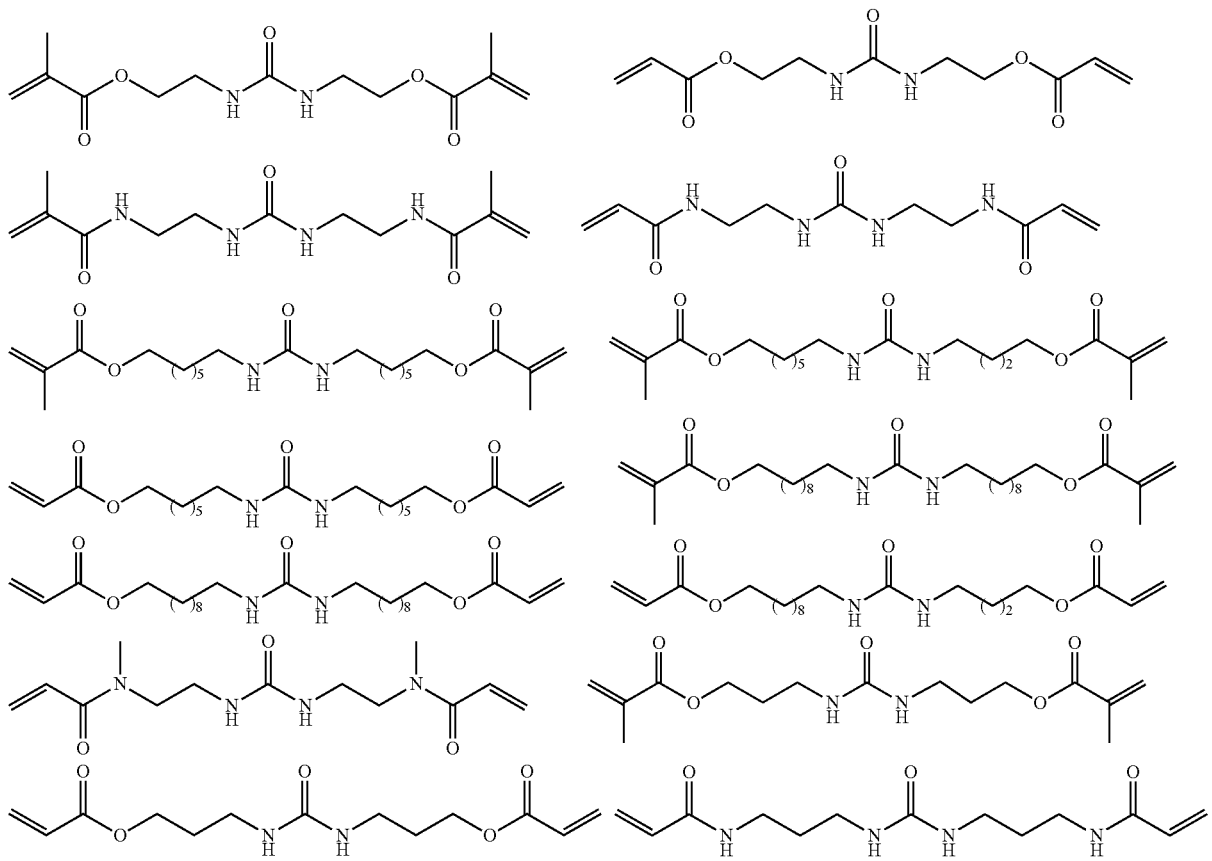

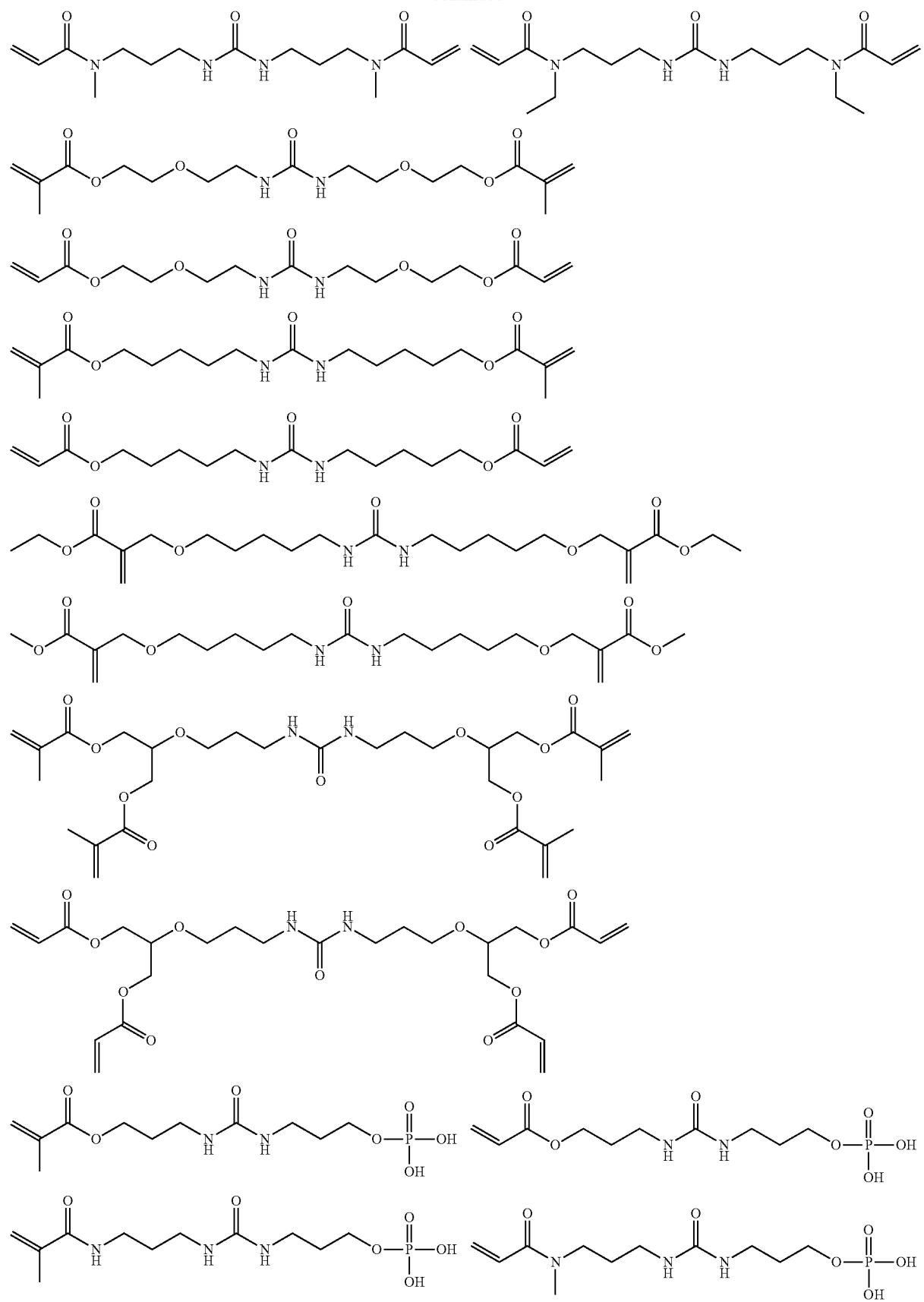

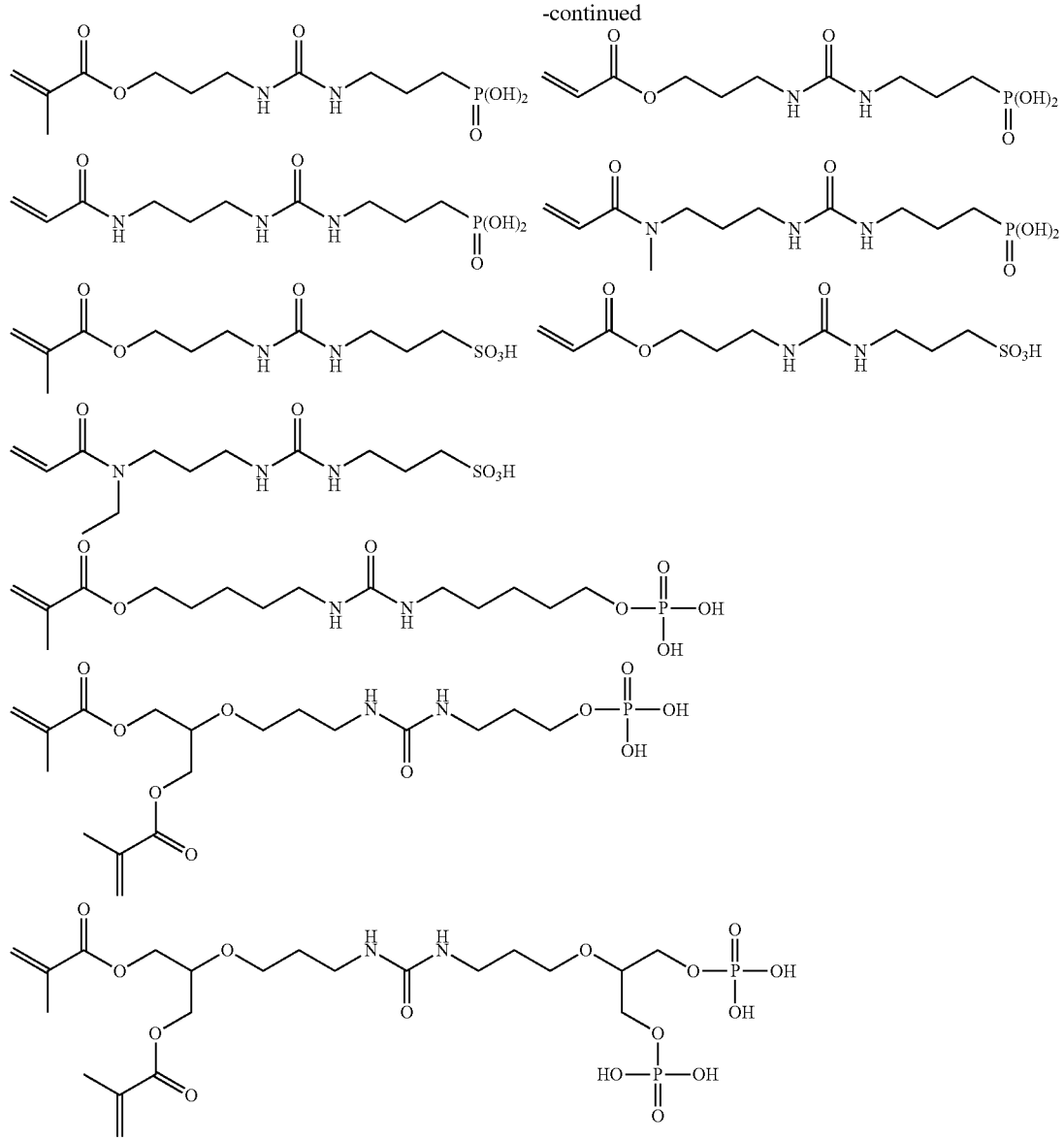

The polymerizable urea derivatives of general formula I are particularly suitable for preparing dental materials, in particular dental materials with self-etching properties, such as adhesives and cements, composites and coating materials. They can be used as adhesion and/or cross-linking components in dental materials. They are very soluble in alcohols, such as e.g. ethanol and isopropanol, and in acetone or in aqueous mixtures thereof.

It has surprisingly been found that solutions of the urea derivatives according to the invention of Formula I do not gel, the urea derivatives are characterized by a very good radical polymerizability. The acidic monomers (Y=acid group) also result in very good bonding values on dentine and in particular on tooth enamel.

The urea derivatives of Formula I are preferably used in a quantity of from 0.1 to 50 wt.-%, particularly preferably 1 to 40 wt.-% and quite particularly preferably in a quantity of from 2 to 30 wt.-% relative to the total mass of the dental material.

The dental materials according to the invention preferably contain further radically polymerizable monomers (comonomers), particularly preferably mono- or polyfunctional (meth)acrylic acid derivatives. By monofunctional monomers are meant monomers with one, by polyfunctional monomers with two or more, preferably two to four, radically polymerizable groups. Examples in this respect are methyl, ethyl, hydroxyethyl, butyl, benzyl, tetrahydrofurfuryl or isobornyl (meth)acrylate, bisphenol A di(meth)acrylate, Bis-GMA (an addition product of methacrylic acid and bisphenol A diglycidyl ether), UDMA (an addition product of 2-hydroxyethyl methacrylate (HEMA) and 2,2,4-trimethyl hexamethylene diisocyanate), di-, tri- or tetraethylene glycol di(meth)acrylate, trimethylolpropane tri(meth)acrylate, pentaerythritol tetra(meth)acrylate, as well as glycerol di(meth)acrylate, 1,4-butanediol di(meth)acrylate, 1,10-decanediol di(meth)acrylate or 1,12-dodecanediol di(meth)acrylate.

A mixture of the named comonomers is preferably used. A mixture which contains 2-hydroxyethyl methacrylate or 2-hydroxypropyl methacrylate mixed with Bis-GMA and/or UDMA, triethylene glycol dimethacrylate or decanediol dimethacrylate is particularly preferred.

Further preferred comonomers are N-mono- or -disubstituted acrylamides, such as e.g. N-ethyl acrylamide, N,N-dimethacrylamide, N-(2-hydroxyethyl)acrylamide or N-methyl-N-(2-hydroxyethyl)acrylamide, or N-monosubstituted methacrylamides, such as e.g. N-ethyl methacrylamide or N-(2-hydroxyethyl)methacrylamide as well as N-vinylpyrrolidone or allyl ether. These monomers are characterized by a high hydrolysis stability and a relatively low viscosity and are therefore suitable for example as diluting monomers.

Likewise preferred comonomers are cross-linking pyrrolidones, such as e.g. 1,6-bis(3-vinyl-2-pyrrolidonyl)-hexane, or commercially available bisacrylamides, such as methylene- or ethylenebisacrylamide, or bis(meth)acrylamides, such as e.g. N,N'-diethyl-1,3-bis(acrylamido)propane, 1,3-bis(methacrylamido)propane, 1,4-bis(acrylamido)butane or 1,4-bis(acryloyl)piperazine, which can be synthesized by conversion from the corresponding diamines with (meth)acrylic acid chloride. These monomers are also characterized by a high hydrolysis stability. They contain two or more radically polymerizable groups and are therefore suitable e.g. as cross-linking monomers.

Finally, mixtures of one or more of the above-named monomers with further radically polymerizable adhesive monomers containing acid groups can also be used. Suitable monomers containing acid groups are polymerizable carboxylic acids, such as maleic acid, acrylic acid, methacrylic acid, 2-(hydroxymethyl)acrylic acid, 4-(meth)acryloyloxyethyl trimellitic anhydride, 10-methacryloyloxydecyl malonic acid, N-(2-hydroxy-3-methacryloyloxypropyl)-N-phenylglycine or 4-vinylbenzoic acid. Examples of suitable phosphonic acid monomers are vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methyl-pentyl phosphonic acid, 2-[4-(dihydroxyphosphoryl)-2-oxa-butyl]-acrylic acid or 2-[4-(dihydroxyphosphoryl)-2-oxabutyl]-acrylic acid ethyl or -2,4,6-trimethylphenyl ester. Examples of suitable acidic polymerizable phosphoric acid esters are 2-methacryloyloxypropyl mono- or dihydrogen phosphate, 2-methacryloyloxyethyl mono- or dihydrogen phosphate, 2-methacryloyloxyethyl phenyl hydrogen phosphate, dipentaerythritol pentamethacryloyloxyphosphate, 10-methacryloyloxydecyl dihydrogen phosphate, phosphoric acid mono-(1-acryloyl-piperidin-4-yl)-ester, 6-(methacrylamido)hexyl dihydrogen phosphate and 1,3-bis-(N-acryloyl-N-propyl-amino)-propan-2-yl-dihydrogen phosphate. Examples of suitable polymerizable sulphonic acids are vinyl sulphonic acid, 4-vinylphenyl sulphonic acid or 3-(methacrylamido)propyl sulphonic acid.

Acidic urea derivatives of Formula I are preferably combined with non-acidic comonomers and non-acidic urea derivatives of Formula I with acidic comonomers or preferably with a mixture of acidic and non-acidic comonomers. In mixtures of acidic urea derivatives of Formula I and non-acidic comonomers, the proportion of non-acidic comonomers preferably lies in the range of from 10 to 300 wt.-% relative to the mass of the acidic urea derivative(s). In mixtures of non-acidic urea derivatives of Formula I and acidic comonomers, the proportion of acidic comonomers preferably lies in the range of from 5 to 100 wt.-% relative to the sum of the masses of non-acidic urea derivatives and optional non-acidic comonomers.

If acidic urea derivatives of Formula I and acidic comonomers are used together, this mixture preferably predominantly and particularly preferably exclusively contains acidic urea derivatives of Formula I.

If cross-linking urea derivatives of Formula I and cross-linking comonomers are used together, this mixture preferably predominantly and particularly preferably exclusively contains cross-linking urea derivatives of Formula I.

To initiate the radical polymerization, the dental materials according to the invention preferably contain an initiator for radical polymerization. Preferably, benzophenone, benzoin and derivatives thereof or α-diketones or derivatives thereof, such as 9,10-phenanthrenequinone, 1-phenyl-propane-1,2-dione, diacetyl or 4,4'-dichlorobenzil, are used for the photopolymerization. Camphorquinone and 2,2-dimethoxy-2-phenyl-acetophenone are preferably used, and α-diketones combined with amines as reducing agents, such as e.g. 4-(dimethylamino)-benzoate, N,N-dimethylaminoethyl methacrylate, N,N-dimethyl-sym.-xylidine or triethanolamine are particularly preferably used. Norrish type I photoinitiators are also particularly suitable, above all acyl bisacyl phosphine oxides, monoacyltrialkyl or diacyldialkyl germanium compounds, such as e.g. benzoyltrimethyl germanium, dibenzoyldiethyl germanium or bis(4-methoxybenzoyl)diethyl germanium. Mixtures of the different photoinitiators can also be used, such as e.g. dibenzoyldiethyl germanium combined with camphorquinone and 4-dimethylaminobenzoic acid ethyl ester.

Redox-initiator combinations, such as e.g. combinations of benzoyl peroxide with N,N-dimethyl-sym.-xylidine, N,N-dimethyl-p-toluidine, N,N-diethyl-3,5-di-tert-butylaniline or N,N-diethanol-p-toluidine, are used as initiators for a polymerization carried out at room temperature. In addition, redox systems consisting of peroxides or hydroperoxides and reducing agents, such as e.g. ascorbic acid, barbiturates, thioureas or sulphinic acids, are also particularly suitable.

The dental materials according to the invention preferably contain a photoinitiator or a combination of a photoinitiator and a redox initiator, preferably a peroxide. A particularly advantageous initiator combination for the dual curing is a mixture of camphorquinone and benzoyl peroxide, wherein these initiators are also preferably combined with an amine.

The compositions used according to the invention furthermore preferably contain organic or inorganic filler particles to improve the mechanical properties or to adjust the viscosity. Fillers for adapting the mechanical properties preferably have an average particle diameter of from 10 nm to 10 μm, preferably from 10 nm to 1.0 μm, fillers for adjusting the viscosity preferably have an average particle diameter of from 10 to 1000 nm, preferably from 10 to 200 nm. These filler types are preferably used together. Unless otherwise stated, the average particle diameter is the weight average value.

Preferred inorganic particulate fillers are amorphous spherical materials based on oxides, such as $ZrO_2$ and $TiO_2$ or mixed oxides of $SiO_2$, $ZrO_2$ and/or $TiO_2$, nanoparticulate or microfine fillers, such as pyrogenic silicic acid or precipitated silicic acid, as well as minifillers, such as quartz, glass ceramic or glass powder with an average particle diameter of from 0.01 to 1 μm as well as radiopaque fillers, such as ytterbium trifluoride or nanoparticulate tantalum(V) oxide or barium sulphate. Preferred organic fillers are fillers based on poly(meth)acrylates, such as e.g. PMMA, or cellulose derivatives, such as e.g. carboxymethylcellulose, which are ground to the above-named particle size after curing. The organic fillers, for their part, can be filled with the named inorganic fillers.

Solvent-containing dental materials represent a further preferred embodiment of the invention. Here, water and polar organic solvents such as acetone, isopropanol and in particular ethanol as well as mixtures of these solvents are preferred. Mixtures of water and polar organic solvents are particularly preferred, more preferably mixtures of water and ethanol, water and acetone or water, ethanol and acetone. Solvent-containing dental materials are particularly suitable for use as adhesives, fissure sealants or coating materials. Adhesives preferably contain isopropanol, ethanol and/or acetone or mixtures of the named solvents with water.

Preferably only the polar organic solvents—without water—are used for fissure sealants or coating materials.

Optionally, the compositions used according to the invention can contain further additives, such as e.g. stabilizers, flavourings, colorants, microbicidal active ingredients, fluoride-ion-releasing additives, optical brighteners, plasticizers and/or UV-absorbers.

The dental materials according to the invention based on polymerizable monomers containing urea groups preferably have the following composition:
a) 0.1 to 50 wt.-%, preferably 1 to 40 wt.-% and particularly preferably 2 to 30 wt.-% polymerizable urea group containing monomer of general formula I,
b) 0.01 to 10 wt.-%, particularly preferably 0.1 to 3.0 wt.-% initiator,
c) 0 to 80 wt.-%, preferably 0 to 60 wt.-% and particularly preferably 5 to 50 wt.-% of one or more other monomers,
d) 0 to 80 wt.-% filler,
e) optionally 0 to 10 wt.-%, preferably 0.1 to 3 wt.-% additive, and
f) 0 to 70 wt.-%, preferably 0 to 60 wt.-% and particularly preferably 0 to 50 wt.-% solvent.

To prepare adhesives, acidic monomers of Formula I can be combined with non-acidic comonomers, non-acidic monomers of Formula I with acidic comonomers, and acidic monomers of Formula I with non-acidic monomers of Formula I.

Dental materials for use as adhesive preferably contain the following components:
a) 0.1 to 50 wt.-%, preferably 1 to 40 wt.-% and particularly preferably 2 to 30 wt.-% urea derivative of general formula I, wherein Y is an acid group,
b) 0.01 to 10 wt.-%, particularly preferably 0.1 to 3.0 wt.-% initiator,
c) 0 to 80 wt.-%, preferably 0 to 60 wt.-% and particularly preferably 5 to 50 wt.-% of one or more other monomers,
d) 0 to 20 wt.-% filler,
e) optionally 0 to 10 wt.-%, preferably 0.1 to 3 wt.-% additive, and
f) 0 to 70 wt.-%, preferably 6 to 60 wt.-% and particularly preferably 10 to 50 wt.-% solvent, preferably water and/or ethanol, isopropanol or acetone.

According to an alternative embodiment, the adhesives preferably contain the following components:
a) 0.1 to 50 wt.-%, preferably 1 to 40 wt.-% and particularly preferably 2 to 30 wt.-% urea derivative of general formula I, wherein Y is a polymerizable group,
b) 0.01 to 10 wt.-%, particularly preferably 0.1 to 3.0 wt.-% initiator,
c1) 0.1 to 50 wt.-%, preferably 1 to 40 wt.-% and particularly preferably 2 to 30 wt.-% of one or more other acidic monomers,
c2) 0 to 80 wt.-%, preferably 0 to 60 wt.-% and particularly preferably 5 to 50 wt.-% of one or more other non-acidic monomers,
d) 0 to 20 wt.-% filler,
e) optionally 0 to 10 wt.-%, preferably 0.1 to 3 wt.-% additive, and
f) 0 to 70 wt.-%, preferably 6 to 60 wt.-% and particularly preferably 10 to 50 wt.-% solvent, preferably water and/or ethanol, isopropanol or acetone.

According to a further alternative embodiment, the adhesives preferably contain the following components:
a1) 0.1 to 50 wt.-%, preferably 1 to 40 wt.-% and particularly preferably 2 to 30 wt.-% urea derivative of general formula I, wherein Y is an acid group,
a2) 0.1 to 50 wt.-%, preferably 1 to 40 wt.-% and particularly preferably 2 to 30 wt.-% urea derivative of general formula I, wherein Y is a polymerizable group,
b) 0.01 to 10 wt.-%, particularly preferably 0.1 to 3.0 wt.-% initiator,
c) 0 to 80 wt.-%, preferably 0 to 60 wt.-% and particularly preferably 5 to 50 wt.-% of one or more other monomers,
d) 0 to 20 wt.-% filler,
e) optionally 0 to 10 wt.-%, preferably 0.1 to 3 wt.-% additive, and
f) 0 to 70 wt.-%, preferably 6 to 60 wt.-% and particularly preferably 10 to 50 wt.-% solvent, preferably water and/or ethanol, isopropanol or acetone.

Dental materials for use as cement or filling material preferably contain the following components:
a) 0.1 to 50 wt.-%, preferably 1 to 40 wt.-% and particularly preferably 2 to 30 wt.-% urea derivative of general formula I, wherein Y is a polymerizable group,
b) 0.01 to 10 wt.-%, particularly preferably 0.1 to 3.0 wt.-% initiator,
c) 0 to 80 wt.-%, preferably 0 to 60 wt.-% and particularly preferably 5 to 50 wt.-% of one or more other monomers,
d) 20 to 80 wt.-% filler, and optionally
e) 0 to 10 wt.-%, preferably 0.1 to 3 wt.-% additive.

Dental materials for use as coating material preferably contain the following components:
a) 0.1 to 50 wt.-%, preferably 1 to 40 wt.-% and particularly preferably 2 to 30 wt.-% urea derivative of general formula I, wherein Y is a polymerizable group,
b) 0.01 to 10 wt.-%, particularly preferably 0.1 to 3.0 wt.-% initiator,
c) 0 to 80 wt.-%, preferably 0 to 60 wt.-% and particularly preferably 5 to 50 wt.-% of one or more other monomers,
d) 0 to 80 wt.-% filler,
e) optionally 0 to 10 wt.-%, preferably 0.1 to 3 wt.-% additive, and
f) 0 to 70 wt.-%, preferably 6 to 60 wt.-% and particularly preferably 10 to 50 wt.-% solvent, preferably ethanol, isopropanol and/or acetone.

Dental materials for use as fissure sealants preferably contain the following components:
a) 0.1 to 50 wt.-%, preferably 1 to 40 wt.-% and particularly preferably 2 to 30 wt.-% urea derivative of general formula I, wherein Y is a polymerizable group,
b) 0.01 to 10 wt.-%, particularly preferably 0.1 to 3.0 wt.-% initiator,
c) 0 to 80 wt.-%, preferably 0 to 60 wt.-% and particularly preferably 5 to 50 wt.-% of one or more other monomers,
d) 0 to 60 wt.-% filler,
e) optionally 0 to 10 wt.-%, preferably 0.1 to 3 wt.-% additive, and
f) 0 to 70 wt.-%, preferably 0 to 60 wt.-% and particularly preferably 0 to 50 wt.-% solvent, preferably ethanol, isopropanol and/or acetone.

Those dental materials that consist of the named components are particularly preferred.

Unless otherwise stated, all percentages relate to the total mass of the composition. The initiator quantity includes all initiator components, such as e.g. the mass of the actual initiator, the reducing agent, etc.

The dental materials according to the invention are particularly suitable for intraoral use by the dentist to restore damaged teeth (clinical dental materials). However, they can also be used extraorally, for example in the preparation or repair of dental restorations (technical dental materials).

The invention is explained in more detail below by means of examples.

EMBODIMENT EXAMPLES

Example 1

Synthesis of 2-[(2-methacryloyloxyethylamino)carbonylamino]-ethylphosphonic acid (MEHEPA)

a) Synthesis of 2-[(2-methacryloyloxyethylamino)carbonylamino]-ethylphosphonic acid diethyl ester 1

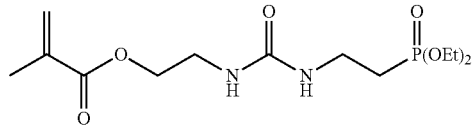

2-Isocyanatoethyl methacrylate (4.7 ml, 33.3 mmol, 1.0 equivalent) was added, accompanied by stirring, dropwise to a solution of 2-aminoethylphosphonic acid diethyl ester (33.3 mmol), which was prepared analogously to the literature (Gali, H.; Prabhu, K. R.; Karra, S. R.; Katti, K. V. J. Org. Chem. 2000, 65, 676-680), in anhydrous methylene chloride (70 ml) at 0° C. The reaction mixture was stirred for 15 min at 0° C. for 2 h at room temperature. The reaction product was concentrated under vacuum and the obtained crude product was purified by flash column chromatography (eluent: ethyl acetate/methanol: 90/10) and resulted in a colourless oil; yield: 98%.

$^1$H-NMR (400 MHz, CDCl$_3$, ppm): δ=1.28 (t, $^3J_{HH}$=7.1 Hz, 6H, POCH$_2$C$\underline{H}_3$); 1.90 (s, 3H, CH$_3$); 1.97 (dt, $^3J_{HH}$=6.6 Hz, $^2J_{HP}$=17.3 Hz, 2H, CH$_2$P); 3.36-3.49 (m, 4H, CH$_2$N); 3.96-4.10 (m, 4H, POC$\underline{H}_2$CH$_3$); 4.16 (t, $^3J_{HH}$=5.6 Hz, 2H, OC$\underline{H}_2$CH$_2$NH); 5.46 (t, $^3J_{HH}$=5.8 Hz, 1H, NH); 5.52-5.55 (m, 1H, C=CH$_2$); 5.75 (t, $^3J_{HH}$=5.8 Hz, 1H, NH); 6.08 (s, 1H, C=CH$_2$).

$^{13}$C-NMR (101 MHz, CDCl$_3$, ppm): δ=16.4 (d, $^3J_{CP}$=6.2 Hz, POCH$_2$$\underline{C}$H$_3$); 18.3 (CH$_3$); 26.2 (d, $^1J_{CP}$=138.4 Hz, CH$_2$P); 34.3 (d, $^2J_{CP}$=5.2 Hz, NH$\underline{C}$H$_2$CH$_2$P); 39.2 (OCH$_2$$\underline{C}$H$_2$NH); 61.8 (d, $^2J_{CP}$=6.5 Hz, PO$\underline{C}$H$_2$CH$_3$); 64.2 (O$\underline{C}$H$_2$CH$_2$NH); 125.8 (C=$\underline{C}$H$_2$); 136.1 ($\underline{C}$=CH$_2$); 158.2 (NHC=O); 167.3 (C=O).

$^{31}$P-NMR (162 MHz, CDCl$_3$, ppm): 30.5.

b) Synthesis of 2-[(2-methacryloyloxyethylamino)carbonylamino]-ethylphosphonic acid (MEHEPA)

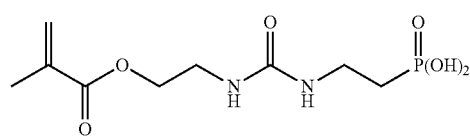

Trimethylsilyl bromide (5.9 ml, 44.6 mmol, 3.0 equivalents) was added to a solution of the corresponding phosphonate 1 (14.9 mmol) in anhydrous methylene chloride (50 ml) and stirred for 5 h at 30° C. The reaction product was then concentrated under vacuum, methanol (50 ml) was added and the mixture was stirred for 30 min at room temperature. After addition of BHT (250 ppm), the solution was concentrated to a constant weight under fine vacuum. MEHEPA was obtained as a highly viscous yellow oil; yield: 100%.

$^1$H-NMR (400 MHz, MeOD, ppm): δ=1.93 (s, 3H, CH$_3$); 1.96-2.07 (m, 2H, CH$_2$P); 3.40-3.50 (m, 4H, CH$_2$N); 4.21 (t, $^3J_{HH}$=5.4 Hz, 2H, OC$\underline{H}_2$CH$_2$NH); 5.63-5.66 (m, 1H, C=CH$_2$); 6.12-6.15 (m, 1H, C=CH$_2$).

$^{13}$C-NMR (101 MHz, MeOD, ppm): δ=18.4 (CH$_3$); 28.9 (d, $^1J_{CP}$=135.8 Hz, CH$_2$P); 36.1 (NH$\underline{C}$H$_2$CH$_2$P); 40.5 (OCH$_2$$\underline{C}$H$_2$NH); 64.7 (O$\underline{C}$H$_2$CH$_2$NH); 126.5 (C=$\underline{C}$H$_2$); 137.5 ($\underline{C}$=CH$_2$); 160.8 (NHC=O); 168.6 (C=O).

$^{31}$P-NMR (162 MHz, MeOD, ppm): 27.1.

Example 2

Synthesis of 6-[(2-methacryloyloxyethylamino)carbonylamino]-hexylphosphonic acid (MEHHPA)

a) Synthesis of 6-phthalimidohexyl-phosphonic acid diethyl ester 2

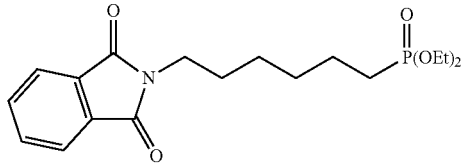

6-Bromohexyl-diethyl phosphonate (15.0 g, 49.8 mmol) was added to a solution of potassium phthalimide (13.8 g, 74.7 mmol, 1.5 equivalents) in DMF (100 ml). The reaction mixture was stirred for 17 h at 100° C. After filtration, the solution was concentrated under vacuum. Ethyl acetate (100 ml) was added to the crude product. The solution was filtered and washed with distilled water (2×100 ml). The organic phase was then dried over anhydrous Na$_2$SO$_4$ and concentrated under vacuum. The obtained crude product was purified by flash column chromatography (eluent: ethyl acetate) and resulted in 13.14 g (35.8 mmol) of the phosphonate 2 as a light yellowish liquid; yield: 72%.

$^1$H-NMR (400 MHz, CDCl$_3$, ppm): δ=1.28-1.48 (m, 4H, CH$_2$); 1.31 (t, $^3J_{HH}$=7.1 Hz, 6H, POCH$_2$C$\underline{H}_3$); 1.53-1.77 (m, 6H, CH$_2$); 3.68 (t, $^3J_{HH}$=7.2 Hz, 2H, CH$_2$N); 4.00-4.15 (m, 4H, POC$\underline{H}_2$CH$_3$); 7.67-7.74 (m, 2H, CH$_{Ar}$); 7.81-7.88 (m, 2H, CH$_{Ar}$).

$^{13}$C-NMR (101 MHz, CDCl$_3$, ppm): δ=16.4 (d, $^3J_{CP}$=6.0 Hz, POCH$_2$$\underline{C}$H$_3$); 22.3 (d, $^2J_{CP}$=5.3 Hz, $\underline{C}$H$_2$CH$_2$P); 25.6 (d, $^1J_{CP}$=140.6 Hz, CH$_2$P); 26.3 (CH$_2$); 28.3 (CH$_2$); 30.1 (d, $^3J_{CP}$=17.1 Hz, $\underline{C}$H$_2$CH$_2$CH$_2$P); 37.8 (CH$_2$N); 61.3 (d, $^2J_{CP}$=6.4 Hz, PO$\underline{C}$H$_2$CH$_3$); 123.1 (CH$_{Ar}$); 132.1 (C$_{Ar}$); 133.8 (CH$_{Ar}$); 168.4 (C=O).

$^{31}$P NMR (162 MHz, CDCl$_3$, ppm): 32.3.

b) Synthesis of 6-aminohexyl-phosphonic acid diethyl ester 3

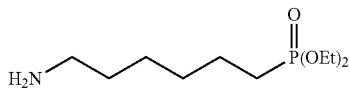

Hydrazine monohydrate (2.66 g, 53.1 mmol, 1.5 equivalents) was added to a solution of the phosphonate 2 (13.0 g, 35.4 mmol) in ethanol (135 ml). The reaction mixture was stirred for 2 h under reflux and concentrated under vacuum. Caustic soda (10 wt.-%, 250 ml) was added to the crude product. The aqueous solution was extracted with methylene chloride (3×200 ml). The organic phases were collected and dried over anhydrous $Na_2SO_4$. After concentration under vacuum, 7.37 g (31.1 mmol) of the amine 3 was isolated as a colourless liquid; yield: 88%.

$^1$H-NMR (400 MHz, $CDCl_3$, ppm): δ=1.25-1.45 (m, 4H, $CH_2$); 1.28 (t, $^3J_{HH}$=7.1 Hz, 6H, $POCH_2CH_3$); 1.51-1.75 (m, 6H, $CH_2$); 2.64 (t, $^3J_{HH}$=7.0 Hz, 2H, $CH_2N$); 3.98-4.13 (m, 4H, $POCH_2CH_3$).

$^{13}$C-NMR (101 MHz, $CDCl_3$, ppm): δ=16.4 (d, $^3J_{CP}$=5.9 Hz, $POCH_2CH_3$); 22.4 (d, $^2J_{CP}$=5.4 Hz, $CH_2CH_2P$); 25.6 (d, $^1J_{CP}$=140.6 Hz, $CH_2P$); 26.4 ($CH_2$); 30.4 (d, $^3J_{CP}$=16.8 Hz, $CH_2CH_2CH_2P$); 33.5 ($CH_2$); 42.1 ($CH_2N$); 61.3 (d, $^2J_{CP}$=6.5 Hz, $POCH_2CH_3$).

$^{31}$P-NMR (162 MHz, $CDCl_3$, ppm): 32.4.

c) Synthesis of 6-[(2-methacryloyloxyethylamino)carbonylamino]-hexylphosphonic acid diethyl ester 4

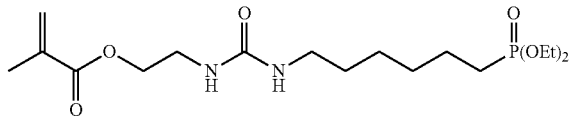

2-Isocyanatoethyl methacrylate (4.7 ml, 33.3 mmol, 1.0 equivalent) was added, accompanied by stirring, dropwise to a solution of the aminophosphonate 3 (33.3 mmol) in anhydrous methylene chloride (70 ml) at 0° C. The reaction mixture was stirred for 15 min at 0° C. and for 2 h at room temperature, concentrated under vacuum and the obtained crude product was purified by flash column chromatography (eluent: ethyl acetate/methanol: 90/10) and resulted in the monomer 4 as a colourless oil; yield: 97%.

$^1$H-NMR (400 MHz, $CDCl_3$, ppm): δ=1.24-1.49 (m, 6H, $CH_2$); 1.29 (t, $^3J_{HH}$=7.1 Hz, 6H, $POCH_2CH_3$); 1.50-1.62 (m, 2H, $CH_2$); 1.63-1.75 (m, 2H, $CH_2$); 1.91 (s, 3H, $CH_3$); 3.11 (q, $^3J_{HH}$=6.8 Hz, 2H, $CH_2N$); 3.45 (q, $^3J_{HH}$=5.6 Hz, 2H, $CH_2N$); 3.96-4.10 (m, 4H, $POCH_2CH_3$); 4.17 (t, $^3J_{HH}$=5.6 Hz, 2H, $OCH_2CH_2NH$); 5.22 (t, $^3J_{HH}$=5.4 Hz, 1H, NH); 5.32 (t, $^3J_{HH}$=5.8 Hz, 1H, NH); 5.53-5.56 (m, 1H, $C=CH_2$); 6.09 (s, 1H, $C=CH_2$).

$^{13}$C-NMR (101 MHz, $CDCl_3$, ppm): δ=16.4 (d, $^3J_{CP}$=6.1 Hz, $POCH_2CH_3$); 18.3 ($CH_3$); 22.2 (d, $^2J_{CP}$=5.2 Hz, $CH_2CH_2P$); 25.2 (d, $^1J_{CP}$=140.4 Hz, $CH_2P$); 26.2 ($CH_2$); 29.7 ($CH_2$); 29.9 (d, $^3J_{CP}$=15.8 Hz, $CH_2CH_2CH_2P$); 39.2 ($CH_2N$); 40.4 ($CH_2N$); 61.5 (d, $^2J_{CP}$=6.6 Hz, $POCH_2CH_3$); 64.4 ($OCH_2CH_2N$); 125.8 ($C=CH_2$); 136.1 ($C=CH_2$); 158.5 ($NHC=O$); 167.4 ($C=O$).

$^{31}$P-NMR (162 MHz, $CDCl_3$, ppm): 32.4.

d) Synthesis of 6-[(2-methacryloyloxyethylamino)carbonylamino]-hexylphosphonic acid (MEHHPA)

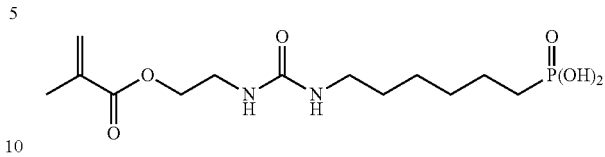

Trimethylsilyl bromide (5.9 ml, 44.6 mmol, 3.0 equivalents) was added dropwise to a solution of the phosphonate 4 (14.9 mmol) in anhydrous methylene chloride (50 ml) and stirred for 5 h at 30° C. The reaction product was then concentrated under vacuum, methanol (50 ml) was added and the mixture was stirred for 30 min at room temperature. After addition of BHT (250 ppm), the solution was dried to a constant weight under fine vacuum and resulted in MEHHPA as a highly viscous yellow oil, yield: 100%.

$^1$H-NMR (400 MHz, MeOD, ppm): δ=1.32-1.68 (m, 8H, $CH_2$); 1.69-1.81 (m, 2H, $CH_2$); 1.94 (s, 3H, $CH_3$); 3.20 (t, $^3J_{HH}$=7.1 Hz, 2H, $CH_2N$); 3.52 (t, $^3J_{HH}$=5.4 Hz, 2H, $CH_2N$); 4.24 (t, $^3J_{HH}$=5.4 Hz, 2H, $OCH_2CH_2NH$); 5.64-5.67 (m, 1H, $C=CH_2$); 6.13 (s, 1H, $C=CH_2$).

$^{13}$C-NMR (101 MHz, MeOD, ppm): δ=17.1 ($CH_3$); 22.2 (d, $^2J_{CP}$=4.8 Hz, $CH_2CH_2P$); 25.9 ($CH_2$); 26.2 (d, $^1J_{CP}$=137.7 Hz, $CH_2P$); 29.0 ($CH_2$); 29.8 (d, $^3J_{CP}$=16.7 Hz, $CH_2CH_2CH_2P$); 39.4 ($CH_2N$); 40.4 ($CH_2N$); 63.0 ($OCH_2CH_2N$); 125.3 ($C=CH_2$); 136.1 ($C=CH_2$); 159.5 ($NHC=O$); 167.2 ($C=O$).

$^{31}$P-NMR (162 MHz, MeOD, ppm): 31.6.

Example 3

Synthesis of 6-[(2-methacryloyloxyethylamino)carbonylamino]-hexyl dihydrogen phosphate (MEHH-DPA)

a) Synthesis of 2-[(6-hydroxyhexylamino)carbonylamino]-ethylmethacrylate 5

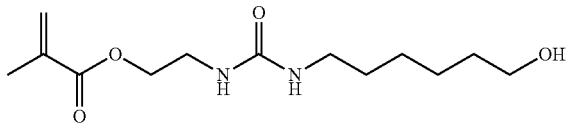 [SMILES: C=C(C)C(=O)OCCNC(=O)NCCCCCCO]

2-Isocyanatoethyl methacrylate (12.1 ml, 85.5 mmol, 1.0 equivalent) was added, accompanied by stirring, dropwise to a solution of 6-aminohexanol (10.0 g, 85.5 mmol) in anhydrous methylene chloride (150 ml) at 0° C. The reaction mixture was stirred for 15 min at 0° C. for 2 h at room temperature. Concentration under vacuum followed, hexane (200 ml) was added to the product and the mixture was stirred for 1 h at room temperature. The solid was separated off by filtration of the suspension and dried under vacuum (0.1 mbar, 1 h). 22.74 g (83.6 mmol) of the alcohol 5 resulted as a white solid; yield: 98%.

$^1$H-NMR (400 MHz, $CDCl_3$, ppm): δ=1.29-1.43 (m, 4H, $CH_2$); 1.45-1.60 (m, 4H, $CH_2$); 1.94 (s, 3H, $CH_3$); 2.08 (s, 1H, OH); 3.15 (q, $^3J_{HH}$=6.4 Hz, 2H, $CH_2N$); 3.49 (q, $^3J_{HH}$=5.6 Hz, 2H, $OCH_2CH_2NH$); 3.62 (t, $^3J_{HH}$=6.4 Hz, 2H, CH$_2$OH); 4.22 (t, $^3J_{HH}$=5.6 Hz, 2H, OCH$_2$CH$_2$NH); 4.79 (t, $^3J_{HH}$=5.5 Hz, 1H, NH); 4.97 (t, $^3J_{HH}$=5.7 Hz, 1H, NH); 5.58-5.61 (m, 1H, C=CH$_2$); 6.12 (s, 1H, C=CH$_2$).

$^{13}$C-NMR (101 MHz, CDCl$_3$, ppm): δ=18.2 (CH$_3$); 23.4 (CH$_2$); 26.5 (CH$_2$); 30.2 (CH$_2$); 32.5 (CH$_2$); 39.2 (CH$_2$N); 40.1 (CH$_2$N); 62.3 (CH$_2$OH); 64.3 (OCH$_2$CH$_2$N); 126.0 (C=CH$_2$); 136.0 (C=CH$_2$); 158.8 (NHC=O); 167.5 (C=O).

b) Synthesis of 6-[(2-methacryloyloxyethylamino) carbonylamino]-hexyldihydrogen phosphate (MEH-HDPA)

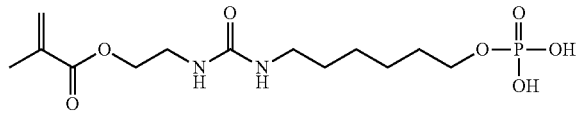 [SMILES: C=C(C)C(=O)OCCNC(=O)NCCCCCCOP(=O)(O)O]

A solution of 22.6 g (83 mmol) monomer 5, 9.24 g (91.3 mmol) triethylamine and 11 mg BHT in 100 ml THF was slowly added dropwise to a solution of 14.0 g (91.3 mmol) phosphorus oxychloride in 200 ml tetrahydrofuran (THF) cooled to −10° C. such that the internal temperature does not exceed −5° C. After two hours of stirring at −10° C., 13.0 g (721 mmol) water was added carefully to the reaction mixture and the batch was stirred for another 15 min at 0° C. The deposited solid was extracted by suction, the filtrate washed 3× in each case with 200 ml saturated saline solution, the organic phase dried with anhydrous sodium sulphate, and then the THF was distilled off on a Rotavapor at 40° C. To draw off residual water, 100 ml acetonitrile was added to the obtained residue and distilled off again on the Rotavapor at 40° C. This process was repeated twice more. 30.2 g MEHHDPA resulted as a brownish, highly viscous oil; yield: 103% (according to the $^1$H-NMR spectrum 3.5 wt.-% THF is still contained).

$^1$H-NMR (400 MHz, DMSO-d$_6$, ppm): δ=1.25-1.39 and 1.52-1.58 (2 m, 6H, 2H, (CH$_2$)$_4$); 1.88 (s, 3H, CH$_3$); 2.97 (t, J=6.9 Hz, 2H, NCH$_2$(CH$_2$)$_4$); 3.27 (t, J=5.6 Hz, 2H, NCH$_2$); 3.78-3.83 (m, 2H, POCH$_2$); 4.05 (t, J=5.6 Hz, 2H, OCH$_2$); 5.68 and 6.06 (2 s, in each case 1H, =CH$_2$); 9.30 (br. s, 2H, OH).

$^{13}$C-NMR (100 MHz, DMSO-d$_6$, ppm): δ=18.4 (CH$_3$); 25.3, 26.4, 30.3 and 30.4 [(CH$_2$)$_4$]; 38.7 and 39.7 (NCH$_2$); 64.6 (OCH$_2$); 65.7 (d, $^2J_{C,P}$=6.0 Hz, POCH$_2$); 126.3 (=CH$_2$); 136.3 (=C); 158.5 (NC=O); 167.0 (C=O).

$^{31}$P-NMR (162 MHz, DMSO-d$_6$, ppm): δ=−1.13.

Example 4

Synthesis of N,N'-bis-(2-methacryloyloxyethyl)-urea (BMAEH)

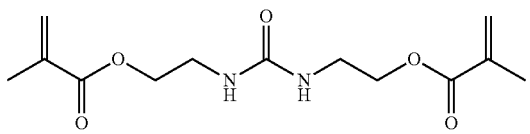 [SMILES: C=C(C)C(=O)OCCNC(=O)NCCOC(=O)C(=C)C]

2-Isocyanatoethyl methacrylate (18.2 ml, 129 mmol) and BHT (5.0 mg) were dissolved in THF (200 mL). Water (13.9 ml, 774 mmol, 6.0 equivalents) was then added and the reaction mixture stirred for 2 h at 60° C. After concentration of the reaction mixture under vacuum, the aqueous residue was extracted with methylene chloride (3×50 ml), the organic phases were collected and dried over anhydrous Na$_2$SO$_4$. Hexane (150 ml) was then added to the crude product, the mixture was stirred for 1 h at room temperature, the solid in the suspension was filtered off and dried under vacuum (0.1 mbar, 1 h). 15.48 g (54.5 mmol) of the compound BMAEH resulted as a white solid; yield: 84%. The monomer is soluble in THF (35 wt.-%) and methanol (50 wt.-%). In both cases, the concentrated solutions did not form a gel.

$^1$H-NMR (400 MHz, CDCl$_3$, ppm): δ=1.92 (s, 6H, CH$_3$); 3.48 (q, $^3J_{HH}$=5.6 Hz, 4H, CH$_2$N); 4.21 (t, $^3J_{HH}$=6.4 Hz, 4H, CH$_2$O); 5.00 (t, $^3J_{HH}$=5.6 Hz, 2H, NH); 5.56-5.59 (m, 2H, C=CH$_2$); 6.10 (s, 2H, C=CH$_2$).

Example 5

Synthesis of N,N'-bis-(2-methacryloyloxyethyl)-urea (BMAHH)

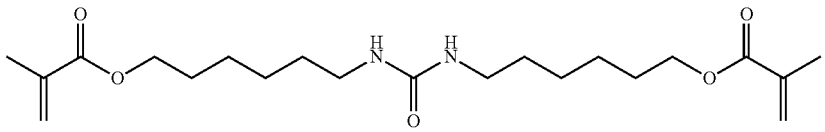 [SMILES: C=C(C)C(=O)OCCCCCCNC(=O)NCCCCCCOC(=O)C(=C)C]

The monomer BMAHH was prepared analogously to the literature (Dubosclard-Gottardi, C.; Caubère, P.; Fort, Y. Tetrahedron 1995, 51, 2561-2572).

Example 6

Investigation of the Photopolymerization of the Urea Monomers MEHEPA and MEHHPA by Means of DSC 0.1 wt.-% of the photoinitiator bis-(4-methoxybenzoyl) diethylgermanium was added to a mixture of the cross-linking agent N,N'-diethyl-1,3-bis(acrylamido)propane (DEPBA) and MEHEPA or MEHHPA in a molar ratio of 8:2. The solution was polymerized in a Diamond Differential Scanning calorimeter (Perkin Elmer) with photopolymerization attachment by irradiation with an LED lamp (Bluephase, Ivoclar Vivadent AG) for 2 min at 37° C. The results are shown in Table 1. The results demonstrate a very good radical copolymerizability of the urea group containing phosphonic acid monomers MEHEPA and MEHHPA, as they do not seriously reduce the polymerization rate or the double bond conversion. This is particularly remarkable in view of the fact that they have only one polymerizable group.

TABLE 1

| Monomer | $t_{max}$ (s) | DC (%) | $R_{pmax}$ (s$^{-1}$) |
| --- | --- | --- | --- |
| DEPBA*) | 2.8 | 62.6 | 0.075 |
| DEPBA/MEHEPA (8/2, mol/mol) | 2.9 | 50.8 | 0.064 |

TABLE 1-continued

| Monomer | $t_{max}$ (s) | DC (%) | $R_{pmax}$ (s$^{-1}$) |
|---|---|---|---|
| DEPBA/MEHHPA (8/2, mol/mol) | 3.1 | 53.6 | 0.061 |

*)comparison
$t_{max}$ = time to reach the maximum polymerization rate
DC = double bond conversion
$R_{pmax}$ = maximum polymerization rate

Example 7

Investigation of the Photopolymerization of the N,N'-bis-(2-methacryloyloxyethyl)urea BMAEH by Means of DSC 0.5 wt.-% of the photoinitiator bis(4-methoxybenzoyl) diethyl germanium was added to a mixture of the 2-hydroxyethyl methacrylate (HEMA) and glycerol dimethacrylate (GDMA) or BMAEH in a molar ratio of 8:2. The solution was polymerized in a Diamond Differential Scanning calorimeter (Perkin Elmer) with photopolymerization attachment by irradiation with an LED lamp (Bluephase, Ivoclar Vivadent AG) for 2 min at 37° C. The results are shown in Table 2. It was shown that the monomer BMAEH is more reactive than GDMA.

TABLE 2

| Monomer | $t_{max}$ (s) | DC (%) | $R_{pmax}$ (s$^{-1}$) |
|---|---|---|---|
| HEMA/GDMA (8/2, mol/mol) | 6.6 | 70.0 | 0.062 |
| HEMA/BMAEH (8/2, mol/mol) | 5.8 | 69.0 | 0.071 |

$t_{max}$ = time to reach the maximum polymerization rate
DC = double bond conversion
$R_{pmax}$ = maximum polymerization rate

Example 8

Adhesives and Adhesion Investigations Based on the Acid Monomers MEHEPA, MEHHPA and MEHHDPA To investigate the dentine and enamel adhesion on bovine teeth, adhesives with the composition given in Table 3 were prepared by mixing the components. Bovine teeth were embedded in plastic cylinders such that the dentine or the enamel and the plastic were in one plane. A layer of adhesive of the above composition was brushed on with a microbrush, the adhesive was moved on the tooth structure for approx. 20 s, briefly blown with an air blower to remove the solvent and exposed to light for 10 s with an LED lamp (Bluephase, Ivoclar Vivadent). A composite cylinder of Tetric® Evo-Ceram (Ivoclar Vivadent) was polymerized onto the adhesive layer. The test pieces were then stored in water for 24 h at 37° C. and the adhesive shear strength was determined according to the ISO guideline "ISO 2003-ISO TR 11405: Dental Materials Guidance on Testing of Adhesion to Tooth Structure" (Table 4). Compared with the 10-methacryloyloxydecylphosphonic acid, a phosphonic acid according to the state of the art, the new urea monomers resulted in a much higher adhesion, in particular tooth enamel.

TABLE 3

Composition of the adhesives (values in wt.-%)

| Component | Adhesive A | Adhesive B | Adhesive C* |
|---|---|---|---|
| MEHEPA (Ex. 1) | 15.0 | — | — |
| MEHHPA (Ex. 2) | — | 15.0 | — |
| MEHHDPA (Ex. 3) | — | — | — |
| MDPA[3] | — | — | 15.0 |
| Bis-GMA[1] | 19.0 | 19.0 | 19.0 |
| DEPBA[4] | 43.2 | 43.2 | 43.2 |
| Aerosil R709[5] | 1.4 | 1.4 | 1.4 |
| Photoinitiator[2] | 2.6 | 2.6 | 2.6 |
| Deionized water | 14.6 | 14.6 | 14.6 |
| Isopropanol | 4.2 | 4.2 | 4.2 |

*)Comparison
[1] Addition product of methacrylic acid and bisphenol A diglycidyl ether
[2] Mixture of camphorquinone (0.9%), 4-dimethylbenzoic acid ethyl ester (0.4%) and 2,4,6-trimethylbenzoyl-diphenylphosphine oxide (Lucerin TPO, 1.3%)
[3] 10-Methacryloyloxydecylphosphonic acid
[4] N,N'-Diethyl-1,3-bis(acrylamido)propane
[5] Methacryl-silanized pyrogenic silicic acid with an average primary particle size of 40 nm (Degussa)

TABLE 4

Dentine and enamel bonding values

| Adhesive | Dentine SBS[1] (MPa) | Enamel SBS[1] (MPa) |
|---|---|---|
| A | 24.5 ± 6.0 (1/5) | 28.5 ± 4.9 |
| B | 28.5 ± 1.9 (2/5) | 31.0 ± 3.5 |
| C* | 22.6 ± 3.4 (0/5) | 16.8 ± 4.6 |

*)Comparison
[1] Shear bond strength

The invention claimed is:

1. Dental material, characterized in that it contains a urea derivative according to general formula I,

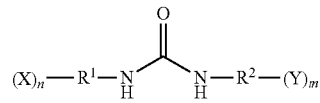

Formula I in which
R$^1$, R$^2$=in each case independently of each other an aliphatic C$_1$-C$_{15}$ radical which can be interrupted by —O—, —S—, —CO—O—,
X=a radically polymerizable group,
Y=PO(OH)$_2$ or —O—PO(OH)$_2$,
n, m=in each case independently of one another 1, 2 or 3.
2. Dental material according to claim 1, wherein X=CH$_2$=CR$^3$—CO—Z— or R$^4$O—CO—C(=CH$_2$)—CH$_2$—Z—, wherein Z is O or NR$^5$ or is absent, R$^3$ is H or CH$_3$ and R$^4$ and R$^5$ are in each case independently of each other H or C$_1$-C$_7$ alkyl.
3. Dental material according to claim 1, wherein R$^1$=an aliphatic C$_2$-C$_{12}$ radical which can be interrupted by —O— or —CO—O—,
R$^2$=an aliphatic C$_1$-C$_{10}$ radical which can be interrupted by —O— or —CO—O—,
X=CH$_2$=CR$^3$—CO—Z— or R$^4$O—CO—C(=CH$_2$)—CH$_2$—Z—, wherein Z is O or NR$^5$, R$^3$ is H or CH$_3$ and R$^4$ and R$^5$ are in each case independently of each other H or C$_1$-C$_3$ alkyl,
n=1 or 2,
m=1 or 2.

4. Dental material according to claim 3, wherein $R^1$, $R^2$=in each case independently of each other a linear aliphatic $C_2$-$C_{10}$ radical which can be interrupted by 1 or 2 —O—, X=$CH_2$=$CR^3$—CO—Z—, wherein Z is O or $NR^5$, or $R^4$O—CO—C(=$CH_2$)—$CH_2$—Z—, wherein Z=O, $R^3$ is H or $CH_3$ and $R^4$ is methyl or ethyl and $R^5$ is H, methyl or ethyl, n, m=in each case 1.

5. Dental material according to claim 1, which additionally contains at least one initiator for radical polymerization.

6. Dental material according to claim 1, which additionally contains at least one further radically polymerizable monomer.

7. Dental material according to claim 6, which contains, as further monomer, one or more mono- or polyfunctional (meth)acrylic acid derivatives and/or (meth)acrylamide derivatives.

8. Dental material according to claim 1, which additionally contains at least one solvent.

9. Dental material according to claim 1, which contains
a) 0.1 to 50 wt.-% urea derivative of general formula I,
b) 0.01 to 10 wt.-% initiator,
c) 0 to 80 wt.-% further monomer,
d) 0 to 80 wt.-% filler,
e) optionally 0 to 10 wt.-% additive,
e) 0 to 70 wt.-% solvent.

10. Dental material according to claim 9 for use as adhesive, which contains 0 to 20 wt.-% filler.

11. Dental material according to claim 9 for use as cement, filling material or coating material, which contains 20 to 80 wt.-% filler.

12. Dental material according to claim 1 for intraoral use.

13. Method of using a dental material according to claim 1 comprising manufacturing or repairing a dental restoration.

14. Dental material according to claim 4, wherein $R^1$ and $R^2$ are identical.

15. Dental material according to claim 8, wherein the solvent comprises water or a mixture of water and a polar organic solvent.

16. Dental material according to claim 9, wherein the additive is present in an amount of 0.1 to 3 wt.-%.

* * * * *